(12) United States Patent
Hall et al.

(10) Patent No.: US 8,343,546 B2
(45) Date of Patent: Jan. 1, 2013

(54) ION EXCHANGE RESIN TREATED TO CONTROL SWELLING

(75) Inventors: Harlan Hall, Oregon, WI (US); J. Scott Madsen, Cottage Grove, WI (US)

(73) Assignee: Coating Place, Inc., Verona, WI (US)

( * ) Notice: Subject to any disclaimer, the term of this patent is extended or adjusted under 35 U.S.C. 154(b) by 1016 days.

(21) Appl. No.: 11/225,834

(22) Filed: Sep. 13, 2005

(65) Prior Publication Data

US 2007/0059270 A1    Mar. 15, 2007

(51) Int. Cl.
*A61K 9/14* (2006.01)

(52) U.S. Cl. .................................... 424/489

(58) Field of Classification Search .............. None
See application file for complete search history.

(56) References Cited

U.S. PATENT DOCUMENTS

| | | | |
|---|---|---|---|
| 4,221,778 A | 9/1980 | Raghunathan | |
| 4,847,077 A | 7/1989 | Raghunathan | |
| 4,859,461 A | 8/1989 | Chow et al. | |
| 4,894,239 A * | 1/1990 | Nonomura et al. | 424/497 |
| 4,996,047 A | 2/1991 | Kelleher et al. | |
| 5,084,287 A | 1/1992 | Ghebre-Sellassie et al. | |
| 5,464,530 A | 11/1995 | Stivers | |
| 6,077,532 A * | 6/2000 | Malkowska et al. | 424/457 |
| 6,280,717 B1 | 8/2001 | Kamakura et al. | |
| 6,569,910 B1 | 5/2003 | Spindler et al. | |
| 2003/0130203 A1 | 7/2003 | Christoph et al. | |
| 2005/0008701 A1 | 1/2005 | Sriwongjanva et al. | |
| 2005/0106247 A1 | 5/2005 | Venkatesh et al. | |
| 2007/0140983 A1 | 6/2007 | Hall et al. | |
| 2007/0148239 A1 | 6/2007 | Hall et al. | |
| 2007/0215511 A1 | 9/2007 | Mehta et al. | |

OTHER PUBLICATIONS

Dowex Ion Exchange Resin, Dow, 1997, 2 pages.
U.S. Appl. No. 11/674,921—Restriction Requirement dated Jan. 14, 2008.
U.S. Appl. No. 11/674,921—Non-final Office Action dated Jun. 9, 2008.
U.S. Appl. No. 11/674,921—Final Office Action dated Nov. 14, 2008.
U.S. Appl. No. 11/674,921—Advisory Action dated Feb. 5, 2009.
U.S. Appl. No. 11/674,921—Non-final Office Action dated Apr. 7, 2009.
U.S. Appl. No. 11/674,940—Restriction Requirement dated Jan. 14, 2008.
U.S. Appl. No. 11/674,940—Non-final Action dated Jun. 10, 2008.
U.S. Appl. No. 11/674,940—Final Office Action dated Nov. 26, 2008.
U.S. Appl. No. 11/674,940—Non-final Office Action dated Jun. 19, 2009.
International Search Report and Written Opinion for PCT/US2006/035739 dated Aug. 10, 2007.
Final Office Action for U.S. Appl. No. 11/674,921 dated Nov. 20, 2009.
Final Office Action for U.S. Appl. No. 11/674,940 dated Mar. 18, 2010.
Non-final Office Action for U.S. Appl. No. 12/965,191, dated Nov. 2, 2011.

* cited by examiner

*Primary Examiner* — Paul Dickinson
(74) *Attorney, Agent, or Firm* — McCarter & English, LLP; Steven G. Davis; Wei Song

(57) ABSTRACT

The present invention provides a method and composition are provided that includes an ion exchange resin treated with from between about 0.01 to about 10 percent by weight of one or more sugar alcohols in contact with one or more ionic pharmaceutically active drug.

12 Claims, No Drawings

ION EXCHANGE RESIN TREATED TO CONTROL SWELLING

TECHNICAL FIELD OF THE INVENTION

The present invention relates general to the controlled release of active agents, and in particular, to pharmacologically active drugs adsorbed to ion exchange resin.

BACKGROUND OF THE INVENTION

Without limiting the scope of the invention, its background is described in connection with ion exchange resins, as an example. Currently, ion exchange resins used in pharmaceutical applications serve a variety of functions, e.g., providing sustained release, masking tastes, eliminating polymorphism, improving the dissolution of poorly soluble drugs, eliminating deliquescence, reducing water uptake, improving stability, reducing abuse liability and improving physical characteristics of pharmacologically active drugs. For example, ion exchange resins are used to prolonged the continuous release of pharmacologically active drugs by absorbing the drug to the ionic exchange resin to form a drug-resin complex. In certain instances, a rate controlling coating is applied to the drug-resin complex.

The sustained release drug-resin complex provides a controlled release of the pharmacologically active drug over a given period of time. Thus, these complexes allow a continuous or intermittent supply of the active drug to a subject. The sustained release drug-resin complex provides a convenient dosage form that provides a therapeutic level of the drug throughout a an extended period. The release of the drug maintains a therapeutically effective plasma level significantly longer than that given by a typical drug dosage form.

In a general sense, an ion exchange resin can be described as an assembly of polymers that contain ionizable groups distributed along the polymer backbone. The polymer has ions that associate with the ionizable groups of the backbone. When the polymer is combined with a solution of counter ions, the counter ions in the solution exchange with the ions of the polymer and the counter ions are physically removed from the solution. Therefore, drug ions (e.g., counter ion) in solution can exchange with the ions of the ion exchange resin (e.g., polymer) through an ionic interaction, as opposed to a covalent interaction. The pharmacologically active drug ions can then be eluted from the ion exchange resin to treat the subject.

A substantial portion of the active drug is ionically bound within the polymer matrix of the ion exchange resin. The active drug elutes from the polymer matrix over time to provide a specific release profile. The size of the adsorbed drug molecule and/or the size of the polymer resin particle (e.g., the cross linkage of the cationic exchange resin) may be altered to control the elution rate. The process of adsorption of a pharmacologically active drug to ion exchange resin is a well-known technique to the skilled artisan and the subject of many United States and foreign patents. Generally, adsorption is accomplished by mixing a pharmacologically active drug and an ion exchange resin an aqueous solution, filtering, drying and optionally coating with a water-permeable diffusion barrier.

U.S. Pat. No. 4,996,047 discloses oral pharmaceutical preparations, which include a pharmacologically active drug bound to an ion-exchange resin to provide a drug-resin complex having a drug content above a specified value. The drug-resin complex is subsequently coated with a water-permeable diffusion barrier coating that is insoluble in gastrointestinal fluids. Thus, the release of drug is controlled under conditions encountered in the gastrointestinal tract.

One of the major disadvantages with the use of an ion exchange resin as a pharmaceutical delivery agent is that ion exchange resin particles are susceptible to swelling. For example, ion exchange resins drug complexes can undergo significant swelling when the dry, non-hydrated drug complex contacts fluids, e.g., water, biological fluids, gastrointestinal fluids. The swelling of the ion exchange resin often ruptures the diffusion barrier coating, which causes a loss of control of the diffusion rate of the drug.

U.S. Pat. No. 4,847,077 discloses sulfonic and cationic exchange resins treated with a critical amount of glycerin to enhance their coatability. The specification discloses methods to achieve prolonged continuous release of a pharmacologically active monobasic drug absorbed on a sulfonic acid cationic exchange resin treated with a critical amount of glycerin. Specifically, the controlled release pharmaceutical preparations containing coated sulfonic acid cationic exchange resin drug complex particles is taught, that are treated prior to coating, with about 15 to 25% by weight of glycerin.

Finally, U.S. Pat. No. 4,221,778 teaches a pharmaceutical preparation containing a diffusion barrier coated ion exchange resin drug complex treated with a solvating agent. The solvating agent retards the rate of swelling in water but does not reduce the overall amount of swelling, only the rate at which swelling occurs.

SUMMARY OF THE INVENTION

The present inventors recognized a need for a pharmacologically active drug-resin complex that does not swell or alter the release rate when contacted with fluids, while reducing the concentration of swelling agent used in the formulations and increasing the compatibility of the swelling reducing agent with pharmacologically active drugs.

The foregoing problems have been recognized for many years and while numerous solutions have been proposed, none of them adequately address all of the problems in a single composition, e.g., controlling the swelling, reducing the concentration of swelling agent, increasing the effectiveness of the swelling controlling agent and increasing the compatibility of the swelling reducing agent with pharmacologically active drugs.

The present inventors have recognized that the nature of the material used as pharmaceutically acceptable ion exchange resins result in the resin undergoing significant swelling (e.g., up to about a 60% increase in volume) when the non-hydrated resin-drug complex is placed in contact with fluids, e.g., water, biological fluid, gastrointestinal fluids. When an ion exchange resin-drug complex is coated with a water-permeable diffusion barrier the swelling of the ion exchange resin often ruptures the diffusion barrier coating. The damage to the water-permeable diffusion barrier coating results in a loss of control of the rate of diffusion of the drug from the resin-drug complex. In addition, the swelling of the ion exchange resin affects the dimensions and shape of the ion exchange resin-drug complex. Additionally, the coating can peel from the resin-drug complex.

In an effort to reduce the swelling of ion exchange resins, the prior art methods teach treating the ion exchange resin-drug complexes with an impregnating agent, e.g., polyethylene glycol, propylene glycol, mannitol, lactose, methylcellulose or propylene glycol. However, the amount of impregnating agents used to control the swelling is dependent on a variety of factors (e.g., the polymer, the solvent composition, the salt concentration, the polarity of the solvent, the degree of cross-linking, the exchange capacity, the strong or weak solvation tendency of the ion groups, the size and extent of the solvation of counter ions, the concentration of the external solution, the extent of the ionic dissociation of functional groups and so forth) and ranges from 15 to 40 percent by weight. For example, one formulation currently used includes Amberlite IR-120 phenylpropanolamine complex with a 35 percent drug loading treated with polyethylene glycol 4000 at about 30 parts by weight of the solvating agent to 100 parts by weight of the resin to reduce swelling.

Specifically, the use of glycols to control the swelling of ion exchange resin drug complexes offers many disadvantages. For instance, the concentration of glycol must be between 15 percent to 40 percent by weight to control the swelling of the ion exchange resin drug complexes; however, even with such concentrations of glycol there remains swelling of the ion exchange resins drug complex. In addition, many compounds are not compatible with glycols, e.g., penicillin, bicitracine, iodine, potassium iodide, tannic acid, and bismuth salts.

In accordance with the present invention, a method and composition are provided that includes an ion exchange resin treated with from about 0.1 percent to about 10 percent by weight of one or more sugar alcohols in contact with one or more ionic pharmaceutically active compounds. Specifically, the ion exchange resin is a cationic exchange resin treated with less than five percent sorbitol to control the subsequent swelling of the drug resin complex, while maintaining a low concentrations of impregnating agents.

For example, the present invention includes a pharmaceutical composition having a pharmaceutically active substance in communication with an ion exchange resin, wherein the ion exchange resin is treated with from about 0.01 percent to about 10 percent by weight of one or more sugar alcohols.

In accordance with the present invention, a method is provided that reduces the swelling of a pharmaceutical composition by contacting one or more cationic exchange resin particles with a solution containing from about 0.01 percent to about 10 percent by weight of sugar alcohol, based on the combined weight of the sugar alcohol and the one or more ionic exchange resin particles.

In addition, the present invention includes a method for preparing a pharmaceutical ion exchange resin drug complex that does not require washing. The method includes contacting one or more grossly wetted cationic exchange resin particles with a drug and adding about 0.1 percent to about 10 percent by weight of one or more sugar alcohols, based on the combined weight of the sugar alcohol, the drug and the one or more grossly wetted ionic exchange resin particles.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention. The present invention may also be used for waste treatment, corrosion control, pesticide release and many other areas using ion-exchange precepts, in both consumer and industrial applications.

A number of definitions are provided herein to facilitate an understanding of the present invention. As used herein, the term "pharmaceutical composition" also means a solution, suspension, cream, ointment, lotion, capsule, caplet, softgel, gelcap, suppository, enema, elixir, syrup, emulsion, film, granule, gum, insert, jelly, foam, paste, pastille, pellet, spray, troche, lozenge, disk, magma, poultice, or wafer and the like.

As used herein, the term "sugar alcohol," "organic polyol," "polyhydric alcohol," "polyalcohol" or "polyol" are used interchangeably to mean non-toxic C2 to C12 linear or branched hydrocarbon having at least 2 hydroxy groups, non-toxic C5 to C12 cyclic or heterocyclic hydrocarbon having at least 2 hydroxy groups, e.g., sorbitol, mannitol, polyglycitol, maltitol, lactitol, isomalt, erythritol, glycerin, polydextrose, fructose, maltose xylitol, 1,3-dihydroxypropane inositol and the carbohydrates such as glucose, sucrose.

The term "immediate release" is used herein to describe a release profile to effect the delivery of an active as soon as possible, that is, as soon as practically made available to a subject, whether in active form, as a precursor and/or as a metabolite. Immediate release may also be defined functionally as the release of over 80 to 90 percent (%) of the active ingredient within about 60, 90, 100 or 120 minutes or less. Immediate release as used herein may also be defined as making the active ingredient available to the subject regardless of uptake, as some drugs may never be absorbed by the animal. Immediate release formulations of the active on a carrier, such as rolled or compressed beads, may be formulated such that the surface area is maximized on beads and the active is exposed immediately. Various immediate release dosage forms may be designed readily by one of skill in art to achieve drug delivery to the stomach and small intestine, depending upon the choice of compression, adhesive materials and/or beading.

The terms "extended release," "controlled release" and "delayed release" as used herein is used to define a release profile to effect delivery of an active over an extended period of time, defined herein as being between about 60 minutes and about 2, 4, 6 or even 24 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the subject regardless of uptake, as some drugs may never be absorbed by the subject. Various extended and delayed release dosage forms may be designed readily by one of skill in art as disclosed herein to achieve delivery to both the small and large intestines, to only the small intestine, or to only the large intestine, depending upon the choice of coating materials and/or coating thickness. As used herein, "a subject" is a patient, animal, insect, mammal or human, who will benefit from the method of this invention.

Pharmaceutical compositions designed for sustained release of active drugs and taste masking commonly use ion exchange resins particles. The present invention provides controlled-release pharmaceutical compositions obtained by complexing a drug with a pharmaceutically acceptable ion-exchange resin, treating with a sugar alcohol and in some cases coating the complex with a substance that will act as a barrier to control the diffusion of the drug from its core complex into the gastrointestinal fluids.

For example, the present invention provide a method and composition that control the swelling of an ion exchange resin particle with one or more ionic pharmaceutically active drug that includes treating with from about 0.01 to about 10 percent by weight of one or more sugar alcohols.

The ion exchange resin particles and pharmacological drug are mixed in an aqueous solution, dried and coated with a water-permeable diffusion barrier. Sorbitol is added to the ion exchange resin-drug complex to control the swelling of the ion exchange resins drug complex upon contact with bodily fluids and in-turn reducing the rupturing and peeling of the coating.

For example, a pharmaceutical composition may have an ionic pharmaceutically active drug that is in communication with an ion exchange resin, wherein the ionic exchange resin has been treated with from about 0.01 to about 10 percent by weight of one or more sugar alcohols, based on the combined weight of the one or more sugar alcohols and the complex particles. Optionally, the pharmaceutical composition may be coated with a water-permeable diffusion barrier coating, whereby a selective, prolonged continuous release of the drug is obtainable under conditions encountered in the gastrointestinal tract.

The present invention includes a pharmaceutical grade cationic ion-exchange resin to bind anionic molecules. Ion exchange resins can be described simply as insoluble polymers that contain ionizable groups distributed regularly along the polymer backbone. As a consequence, any counter ion associated (e.g., drug) with the ion exchange resin is ionically bound to the ion exchange resin and physically separated from the surrounding fluid.

The cationic exchange resin of the present may be strongly or weekly acidic and have a variety of functional groups, e.g., weakly acidic type of resin containing carboxylic acid group, or strongly acidic type of resins containing sulfonic functional groups. Generally, the carboxylic functional groups are derived from polymers or copolymers of methacrylic acid or polymethacrylic acid and the sulfonic functional groups are generally derived from polymers or copolymers of styrene and divinylbenzene. Other polymeric matrices, organic ion exchange matrices or inorganic ion exchange matrices may be used as suitable ion exchange resins, e.g., methacrylic, acrylic and phenol formaldehyde.

In addition, ion exchange agents may be used in conjunction with polymer matrices (e.g., cellulosic or dextran) to form a suitable ion exchange resin. In one embodiment of the present invention, the ionic exchange resin is a sulfonic acid cationic exchange resin. The present invention also uses a sulphonic acid cation exchange resin, which includes phenolsulphonic acid cation exchange resins and carboxylic-sulphonic acid cation exchange resins. Generally, the resin salt is obtained from the reaction of a sulphonic acid with an alkali, e.g., amine. The basic sulphonic acid cation exchange resin has a cation of an amphetamine adsorbed thereon. The skilled artisan will recognize that other cationic exchange resins may be used.

Similarly, a wide range of cationic (for the basic drugs) or anionic (for the acidic drugs) exchange resins can be used to form ion exchange resin drug complexes. In general, ionexchangers suitable for use in ion-exchange chromatography and for such applications as deionization of water are suitable for use as controlled release drug preparations. For examples, a model large ion exchange particle includes the cationic exchange resin Amberlite® IR-120 having a 20-30 mesh spherical particles and a model small ion exchange particle resin includes Amberlite® XE-69 with a 100-200 mesh fractured resin particles of Amberlite® IR-120. The parent resin of Amberlite® IR-120 and Amberlite® XE-69 is described by the manufacturer as gel-type divinylbenzene sulfonic acid cation exchange resin that swells in water. Other suitable ion exchange resin candidates include synthetic ion exchange resins with different polymeric matrices (e.g., methacrylic, acrylic, phenol formaldehyde), ion exchange agents with cellulosic or dextran polymer matrices and inorganic ion exchange matrices.

The ionic exchange resin includes sulfonic acid cationic exchange resin and may be made from a polyester polymer containing sulphonic groups, additionally containing units derived from ethylene glycol, units derived from tri- and tetraethylene glycol and units derived from terephthalate, neutralized polyesters having a terminal amine functional group, polyester block copolymers, block copolymers of phthalic and sulphonphthalic acid/ethylene glycol/polymethyl siloxane α,γ-hydroxypropyl and vinyl acetate/vinyl butylbenzoate/crotonic acid. In addition, the polymer resin may be crosslinked. The crosslinkers include poly(2-acrylamido-2-methylpropanesulphonic acid) polymer with one monomer containing at least two olefinic double bonds, e.g., dipropylene glycol diallyl ether, polyglycol diallyl ether, triethylene glycol divinyl ether, hydroquinone diallyl ether, tetraallyloxyethanoyl, allyl ether, vinyl ether, a polyfunctional alcohol, tetraethylene glycol diacrylate, triallylamine, trimethylolpropane diallyl ether, methylenebisacrylamide or divinylbenzene.

Representative pharmaceutical grade ion exchange resins for use in accordance with the present invention are known to those skilled in the art. For example, pharmaceutical grade ion exchange resins are commercially available, e.g., the Rohm and Haas company and Dow Corning, e.g., Amberlite® IR-20, Amberlite® IRP-69, Amberlite® IRP-64, Amberlite® IRP-58, Amberlite® IRC-50, Amberlite® IRP-69 and Dow® XYS-40010.00, Dow® XYS-40013.00, etc. The pharmaceutical grade cationic ion-exchange resins may include particles of varying size ranges, and as either a monodisperse or a polydisperse mixture. The ion exchange resin particles may range in size from 40 to 1500. In one example, the gel-type divinylbenzene sulfonic acid cation exchange resin Amberlite® IRP-69 consisting of 100-200 mesh was used.

In general, all acidic and basic drugs, especially those having short biological half-lives in the order of up to about 12 hours, are potential candidates for inclusion in the present invention. Many drugs exist in the free acid, free base, and a salt form. For example, a base drug may exist as either a free base form or a salt form, e.g., a base drug, lidocaine has an amine free base form and a hydrochloride acid addition salt form. Conversely, an acid drug may exist in either a free acid form or in the form of a salt made by reacting the free acid with a base, e.g., salicylic acid exists as a salt, typically as sodium salicylate. For example, a cationic resin interacts with the basic nitrogen group of an organic molecule. Generally, the functional groups on the drug dictate the interaction with the ion exchange resin, and thus, influence the adsorption and the elution characteristics of the drug. A substantial portion of the active drug is adsorbed within the polymer matrix and elutes therefrom. To control the elution rate the size of the particle and the size of the adsorbed drug may be altered by modifying the cross linkage of the ion exchange resin.

Suitable pharmaceutically active drugs include narcotic analgesics, (e.g., codeine, dihydrocodeine, hydromorphone, morphine, pentazocine and propoxyphene), sympathomimetics, (e.g., norephedrine and pseudoephedrine), antitussives, (e.g., dextromethorphan, gauifenesin), analgesics, (e.g., aspirin and tramadol), antiemetics, (e.g., metoclopramide), anticholinergics, (e.g., atropine, ipratropium bromide and scopolamine), muscle relaxants, (e.g., cyclobenzaprine and papaverine), bronchodilators, (e.g., salbutamol, terbutaline and theophylline), antibiotics, (e.g., amoxycillin, ampicillin, azlocillin, bacampicillin, cefamandole, cefonicid, cefotaxime, cefotetan, cefoxitin, ceftriaxone, mezlocillin and piperacillin), antidepressants, (e.g., bupropion, nomifensine, and nortriptyline), antiasthmatics, (e.g., cromolyn), antineoplastics, (e.g., tamoxifen), antiepileptics, (e.g., valproic acid and phenvtoin), cardiovascular agents, (e.g., propranolol) phenylephrine, and gauifenesin. Acid addition salts or if appropriate, alkali or alkaline earth metal salts of the above drugs would be particularly suitable for use in the present invention. Specific examples of suitable pharmaceutically active drugs include but not limited to dehydrocholic acid, diflunisal, ethacrynic acid, fenoprofen, furosemide, gemfibrozil, ibuprofen, naproxen, phenyloin, probenecid, sulindac, theophylline, salicylic acid, acetylsalicylic acid, acetophenazine, amitriptyline, amphetamine, benztropine, biperiden, bromodiphenhydramine, brompheniramine, carbinoxamine, chlorcyclizine, chlorpheniramine, chlorphenoxamine, chlorpromazine, clemastine, clomiphene, clonidine, codeine, cyclizine, cyclobenzaprine, cyproheptadine, desipramine, desloratadine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, loratadine, maprotiline, meclizine, mepenzolate, meperidine, mephentermine, mesoridazine, methadone, methdilazine, methscopolamine, methysergide, metoprolol, nortriptyline, noscapine, nylindrin, orphenadrine, papaverine, pentazocine, phendimetrazine, phentermine, phenylephrine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine, codeine, aminocaproic acid, aminosalicylic acid, hydromorphone, isoxsuprine, levorphanol, melphalan, morphine, nalidixic acid, paraminosalicylic acid and mixtures and combinations thereof.

Examples of acidic and basic drugs that may be used with the present invention include phenylpropanolamine (PPA), dextromethorphan, ephedrin, pseudoephedrine, paraamino salicyclic acid, acetyl salicylic acid, phentermine (phenyltertiary-butyl-amine) and acetaminophen. The skilled artisan will recognize the variety of drugs and resins that may be used and the modifications to alter the polymer, copolymer, cross linking agent that may be used to alter the characteristics of the drug-resin complex. The pharmaceutically active compounds useful in the practice of the present invention include antihistamines, decongestants, antitussives and/or expectorants. Other drugs for use with the present invention include, but are not limited to non-steroidal anti-inflammatory drugs (NSAIDs) and other analgesic drugs, e.g., acetaminophen and phenacetin. These materials are incorporated into the immediate or controlled release formulations of the invention in amounts governed by the desired release characteristics of the material in such excipient base and such that conventional dosages comply with applicable FDA or other regulations. The drug may be loaded in a specific concentration to allow the specific release of the drug over a given time range. In general, the maximum concentration of bound drug may be in excess of about 60%; however, ranges between about 1% and about 50% are contemplated with the present invention.

The present invention may be used to deliver bioactive agents including pharmaceuticals and drugs, bioactive synthetic organic molecules, genetic materials, proteins, peptides, polypeptides, vitamins, steroids, polyanionic agents, genetic material, and diagnostic agents. Bioactive vitamins, steroids, proteins, peptides and polypeptides can be of natural origin or synthetic. Exemplary polyanionic agents include but are not limited to sulphated polysaccharides, negatively charged serum albumin and milk proteins, synthetic sulphated polymers, polymerized anionic surfactants, and polyphosphates. Suitable diagnostic agents include but are not limited to dyes and contrast agents for use in connection with magnetic resonance imaging, ultrasound or computed tomography of a patient. In addition, the pharmaceutically active drug may be any pesticide known to the skilled artisan for use in the extended release pesticide control of insects, rodents and other pests.

Suitable genetic material includes nucleic acids, nucleosides, nucleotides, and polynucleotides that can be either isolated genomic, synthetic or recombinant material; either single or double stranded; and either in the sense or antisense direction, with or without modifications to bases, carbohydrate residues or phosphodiester linkages. Exemplary sources for the genetic material include but are not limited to deoxyribonucleic acids (DNA), ribonucleic acids (RNA), complementary DNA (cDNA), messenger RNA (mRNA), ribosomal RNA (rRNA), short interfering RNA (siRNA), ribozymes, and mixed duplexes and triplexes of RNA and DNA.

Genetic materials are genes carried on expression vectors including but not limited to helper viruses, plasmids, phagemids, cosmids, and yeast artificial chromosomes. The genetic material suitable for the present invention is capable of coding for at least a portion of a therapeutic, regulatory, and/or diagnostic protein. Moreover, genetic materials can preferably code for more than one type of protein. For example, a bioactive agent may include plasmid DNA having genetic material encoding therapeutic protein and a selectable or diagnostic marker to monitor the delivery of the plasmid DNA, e.g., pDsRed-human insulin promoter. Such proteins include but are not limited to histocompatibility antigens, cell adhesion molecules, growth factors, coagulation factors, hormones, insulin, cytokines, chemokines, antibodies, antibody fragments, cell receptors, intracellular enzymes, transcriptional factors, toxic peptides capable of eliminating diseased or malignant cells. Other genetic materials that could be delivered by this technique included adenovirus, adeno-associated virus, retrovirus, lentivirus, RNA, siRNA, or chemicals that selectively turn on or off specific genes, such as polyamides or peptide fragments. Modifications to wild-type proteins resulting in agonists or antagonists of the wild type variant fall in the scope of this invention. The genetic material may also include a tissue-specific promoter or expression control sequences such as a transcriptional promoter, an enhancer, a transcriptional terminator, an operator or other control sequences.

Examples of active agents for use with the present invention include, but are not limited to, hormone products such as, vasopressin and oxytocin and their derivatives, glucagon and thyroid agents as iodine products and anti-thyroid agents; cardiovascular products as chelating agents and mercurial diuretics and cardiac glycosides; respiratory products as xanthine derivatives (theophylline and aminophylline); anti-infectives as aminoglycosides, antifungals (e.g., amphotericin), penicillin and cephalosporin antibiotics, antiviral agents (e.g., zidovudine, ribavirin, amantadine, vidarabine and acyclovir), antihelmintics, antimalarials, and antituberculous drugs; biologicals such as antibodies (e.g., antitoxins and antivenins), vaccine antigens (e.g., bacterial vaccines, viral vaccines, toxoids); antineoplastics (e.g., nitrosoureas, nitrogen mustards, antimetabolites (fluorouracil, hormones, progestins and estrogens agonists and/or antagonists); mitotic inhibitors (e.g., etoposide and/or vinca alkaloids), radiopharmaceuticals (e.g., radioactive iodine and phosphorus products); and interferon, hydroxyurea, procarbazine, dacarbazine, mitotane, asparaginase and cyclosporins, including mixtures and combinations thereof.

Other suitable therapeutics include, but are not limited to: thrombolytic agents such as urokinase; coagulants such as thrombin; antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adsnine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicinhydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), erwinaasparaginase, etoposide (VP-16), interferon alpha-2a, interferon alpha-2b, teniposide (VM-26), vinblastine sulfate (VLB), vincristine sulfate, bleomycin, bleomycin sulfate, methotrexate, adriamycin, and arabinosyl; blood products such as parenteral iron, hemin; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungalagents such as ketoconazole, nystatin, griseofulvin, flucytosine (5-fc), miconazole, amphotericin B, ricin, and beta-lactam antibiotics (e.g., penicillin, ampicillin, sulfazecin); hormones such as growth hormone, PDGF, EGF, CSF, GM-CSF, melanocyte stimulating hormone, estradiol, beclomethasone dipropionate, betamethasone, betamethasone acetate and betamethasone sodium phosphate, vetamethasonedisodiumphosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisoloneacetate, prednisolone sodium phosphate, prednisolone rebutate, prednisone, triamcinolone, triamcinolone acetonide, triamcinolone diacetate, triamcinolone hexacetonide and fludrocortisone acetate; vitamins such vitamin C, E, A, K, ascyanocobalamin, neinoic acid, retinoids and derivatives such as retinolpalmitate, and alpha-tocopherol(s); peptides (e.g., T cell epitopes such as MAGE, GAGE, DAGE, etc.); proteins, such as manganese super oxide dimutase, alcohol dehydrogenase, nitric oxide synthase; enzymes such as alkaline phosphatase; anti-allergic agents' such as amelexanox; anti-coagulation agents such as phenprocoumon and heparin; circulatory drugs such as propranolol; metabolic potentiators such asglutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), Ribavirin andvidarabine monohydrate (adenine arabinoside, ara-A); antianginals such asdiltiazem, nifedipine, verapamil, erythrityl tetranitrate, isosorbidedinitrate, nitroglycerin (glyceryl trinitrate) and pentaerythritoltetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocainehydrochloride, lidocaine hydrochloride, mepivacaine hydrochloride, procainehydrochloride and tetracaine hydrochloride; general anesthetics such asdroperidol, etomidate, fentanyl citrate with droperidol, ketaminehydrochloride, methohexital sodium and thiopental sodium; and radioactive particles or ions such as strontium, iodide rhenium and yttrium, and combinations and mixtures thereof.

The ion exchange resin is treated with one or more sugar alcohols. The ion exchange resin may be treated before, during or after the addition of the pharmaceutical drug and formation of the drug-resin complex. Additionally, the drug-resin complex may be treated before, during or after the addition of a coating to the drug-ion exchange resin complex. The sugar alcohol may be added as a solid, liquid or gel. The sugar alcohols may be in an aqueous solution or mixtures containing varying amounts of organic compounds known to those skilled in the art. Furthermore, when more than one sugar alcohol is used the sugar alcohols may be similar or different depending on the particular application and conditions. In some embodiments, the ionic exchange resin may be treated with between about 1 to 10 percent by weight of sorbitol, based on the combined weight of the sorbitol and the drug-resin particles. Other concentrations of sorbitol may be used including about 0.1% to about 5% by weight.

The sugar alcohols may be of many types known to persons of skill in the art to control the swelling of the pharmaceutical grade ion exchange drug-resins complex. The sugar alcohol is generally sorbitol; however, polyhydric alcohols such as mannitol; sorbitol; xylitol; maltitol; lactitol, 1,3-dihydroxypropane, or other non-toxic C2 to C12 linear or branched hydrocarbon having at least 2 hydroxy groups known to the skilled artisan may be used. Additionally, non-toxic C5 to C12 cyclic or heterocyclic hydrocarbon having at least 2 hydroxy groups (e.g., inositol and the carbohydrates such as glucose, sucrose) may be used as well. The sugar or the sugar alcohol present in the solution has a molecular weight of from 90 to 550, and especially from molecular weights of between 150 and 370. The sugars are monosaccharides or disaccharides and reduced monosaccharides or disaccharides and substituted monosaccharides or disaccharides. Suitable sugars/sugar alcohols are sucrose, dextrose, maltose, fructose, lactose, mannitol, sorbitol or xylitol.

The general method for preparing controlled release cationic exchange resin drug complex using the present invention involves: (i) preparation of an ion exchange resin drug complex; (ii) treating the ion exchange resin drug complex with a suitable sugar alcohol; and (iii) drying the treated ion exchange resin drug complex. The ion exchange resin drug complex may be optionally coated with a water-permeable diffusion barrier.

Preparing the ion exchange resin drug complex from the ion exchange resin is generally includes mixing the ion exchange resin with a solution in the presence of a polyalcohol and allowing sufficient time for loading. The resin/fluid slurry is filtered. Unlike methods currently used in the art it is not necessary to wash the ionic exchange resin-complex after the additions. Furthermore, the present invention provides for equilibrium redistribution by allowing the unbound drug, the free drug or any water soluble swelling agent to redistribute themselves in equilibrium. The equilibrium distribution allows the free drug to be further taken up by the resin.

For example, the present invention includes a method of making a pharmaceutical composition by contacting one or more ion exchange resin particles and one or more pharmaceutically active drugs to form a cationic exchange resin pharmaceutically active drugs complex. The ionic exchange resin drug complex is treated to control the swelling of the resin by adding one or more sugar alcohols. The one or more sugar alcohols make up between about 0.01% and about 10% by weight of one or more sugar alcohols, based on the combined weight of the sugar alcohol, the drug(s) and the one or more ionic exchange resin particles. The composition may then be formulated into the desired pharmaceutical composition delivery forms.

Generally, the present invention is formulated into a liquid, gel, tablet, caplet, or capsule; however, other pharmaceutical composition delivery forms may be use, while taking advantage of the present invention. Other agents may be added including binders, lubricants, diluents, disintegrating agents, coloring agents, sweeteners, flavoring agents, preservatives and flow-inducing agents. The tablets can be compressed, multiple compressed, tablet triturates or coated, e.g., enteric coating, sugar coating, or film coating. When in the form of a liquid, the liquid oral dosage may be in the form of aqueous and nonaqueous solutions, emulsions, suspensions, and solutions granules, containing suitable, emulsifying agents, solvents, preservatives, suspending agents, diluents, sweeteners, coloring agents, and flavoring agents.

The present invention provides a method of preparing a resin drug complex without washing. Preparing the ion exchange resin drug complex from the ion exchange resin includes mixing the ion exchange resin with a solution and allowing sufficient time for loading. The resin/fluid slurry is filtered. Unlike methods currently used in the art, it is not necessary to wash the ionic exchange resin-complex.

The present invention also provides a method of controlling the swelling of a pharmaceutical composition by contacting one or more cationic exchange resin particles with about 0.01% to about 10% by weight of sugar alcohol, based on the combined weight of the sugar alcohol, the drug(s) and the one or more ionic exchange resin particles.

In accordance with the present invention, it is necessary to combine the sugar alcohol with the ion exchange resin to form a mixture (e.g., slurry). Generally, the mixture is an aqueous solution; however, other solutions, compositions or mixtures are acceptable. The ratio of ion exchange resin to sugar alcohol is from about 1:1 to about 50:1, i.e., from about 1 gram of resin per gram of the sugar alcohol to about 1 gram of resin per 20 mg. of polyol. Other ratios may be used depending on the method of incorporation and the particular sugar alcohol and resin, e.g., about 1:0.01 to about 5:0.01, about 0.01:1 to about 0.01:5, and combinations thereof. In Example I, the ratio of the amount of ion exchange resin in suspension to the amount of sugar alcohol is about 1.7:1 (e.g., 300 gram of resin per 175 gram of molecule) with most of the sugar alcohol not remaining in the product. In another example, the concentration of the sugar alcohol is between about 1 and 10% by weight, i.e., about 10 mg to about 100 mg of molecule.

Example I

| Resin | 300 g |
|---|---|
| Drug | 300 g |
| 70% Sorbitol | 250 mL |
| Purified Water | 750 mL |

In Example I, the water, sorbitol, drug and resin are slurried together and sufficient time is allowed for the drug to load onto the resin. When the loading operation is completed the components of the slurry are separated (e.g., filtered or centrifuged) into liquid and solid fractions. Because the sugar alcohol is highly water soluble most of the sugar alcohol remains in the aqueous phase, leaving about 4% sorbitol in the solids. The solids are not washed, but are dried to yield material suitable for coating.

Example II

| Resin | 300 g |
|---|---|
| Drug | 300 g |
| Sorbitol | 7.5 g |
| Purified Water | 992.5 mL |

In Example II, the water, drug and resin are slurried together and sufficient time is allowed for the drug to load onto the resin. When the loading operation is completed the slurry is separated (e.g., filtered or centrifuged) into liquid and solid fractions. The liquid fraction is discarded. The solid fraction is not washed and is dried. Sorbitol is dissolved in 100 grams water, added to the dried drug resin complex and the drug resin complex is allowed to absorb the sorbitol solution. The treated resin may then be dried and coated.

To form the cationic exchange resin drug complex it is necessary to combine an ion exchange resin with one or more molecules, e.g., one or more ionic drug compounds. The adsorption of molecules to the surface of a resin is well known to persons of skill in the art. In addition, the ionic drug molecule may be attached to a linker that allows attachment of the drug to the ion exchange resin via the linker. The combination of ion exchange resins and drug may be in the form of a slurry or other mixture, depending on the particular application. In addition, a coating may be applied to the drug-resin complex. The mixture (e.g., an admixture of a slurry of the ion exchange resin, the drug and the sugar alcohol) may be dried to remove the water. The drying may be carried out using methods know to the skilled artisan including conventional means, i.e., filtered, dried over a purge of nitrogen, under vacuum, in a fluid bed, in an oven, etc.

The present invention optionally includes a pharmacologically active drug-resin complex coated to prolong the continuous release of drugs, under harsh biological conditions, e.g., such as those encountered in the gastrointestinal tract. Conventional coating solvents (e.g., ethanol, a methylene chloride/acetone mixture or other component known to the skilled artisan) or aqueous based coatings and procedures can be employed to coat the ion exchange resin drug complex. In one illustrative example, air suspension spray coating techniques may be carried out using a Wurster coating apparatus. However, other techniques may be used to coat the particle including other types of fluid bed spray, coacervation, solvent evaporation or other methods known to persons of skill in the art. Generally, the coating is applied to the drug-resin complex. Alternatively, the coating can be applied to the resin before complexing with the drug.

Particle coating. Another example of a coated particle of the present invention provides a selective, prolonged continuous release of pharmacologically active drugs, under conditions such as those encountered in the gastrointestinal tract by the application of a diffusion barrier coating to an ion exchange drug-resin complex treated with a solvating agent. Another prolonged release formulation of the present invention includes the addition of a second ionic substance (e.g., a combination drug, a dye, a dispersing agent or the like) having the same ionic charge as the drug on the drug-resin complex by employing the second ionic substance in the ion form of an exchange resin complex. The manufacture of a formulation of any drug for liquid dosage usage requires that the final formulation have the drug dissolved or suspended in a liquid that possess extended shelf-life stability and exhibit no change in active drug dosage level over a period of time and has acceptable taste. Thus, to prepare a liquid formulation of any type drug it may be necessary to employ extenders such as water or syrup and to add flavors, sweeteners, thickening agents, dyes and the like. To control the dissolution profile of the formulation versus the dissolution profile of the same drug in water, the coated particles may also be included in the presence of ionic substances bearing the same ionic charge as the sustained release drug present in the formulation as a coated drug-resin complex. The second ionic material need not be coated with the water-permeable diffusion barrier coating.

The water-permeable, diffusion barrier coating materials can be any of the conventional synthetic or natural film-forming materials with diffusion barrier properties and with no inherent pharmacological or toxic properties. For example, ethylcellulose, a water insoluble film-forming agent, may be used as a diffusion barrier membrane material. A plasticizer, (e.g., Durkex 500 vegetable oil) may be used to improve the film forming characteristics of ethylcellulose and/or to alter the permeability characteristics of the film. The amount of coating used depends on the degree of drug release prolongation desired and is a function of particle size, drug solubility, film permeability and other factors. By varying the amount of coating, and/or by blending coated drug-resin complex with uncoated drug-resin complex, and/or blending different coatings it is possible to selectively modify the preparation's drug dissolution profile as desired.

In general, the major components of the coating should be insoluble in, and permeable to, water. Alternatively, a water-soluble substance, such as methyl cellulose may be incorporated, to alter the permeability of the coating, or an acid-insoluble, base-soluble substance to act as an enteric coating may be used. The water-permeable diffusion barrier will generally include a water insoluble material such as a wax, a fatty alcohol, shellac, zein, shellac, polyvinylpyrrolidone, a water insoluble cellulose derivative, ethyl cellulose, a polymethacrylate, or methyl cellulose. The coating materials may be applied as a solution or suspension in an aqueous fluid or as a solution in organic solvents. In some instances, the present invention may include a water-permeable diffusion barrier in contact with at least a portion of the ionic pharmaceutically active drug in communication with an ionic exchange resin.

Example III

The water-permeable diffusion barrier coated drug resin complex includes:

| | |
|---|---|
| Drug Resin Complex | 2000 g |
| Ethylcellulose | 300 g |
| Ethyl acetate | 5700 g |

The drug resin complex was placed in a fluid-bed coating apparatus and fluidized with intake air. The ethylcellulose was dissolved in the ethyl acetate and applied at a rate of about 20-25 grams per minute until 6000 g had been applied. Fluidization was continued with the heated air for an additional ten minutes after termination of the application of the coating solution.

Example IV

Another water-permeable diffusion barrier coated drug resin complex includes:

| | |
|---|---|
| Drug Resin Complex | 2000 g |
| Ethylcellulose | 119 g |
| Myvacet | 11 g |
| Ethanol | 2470 g |

The drug resin complex was placed in a fluid-bed coating apparatus and fluidized with intake air. The myvacet was dissolved in the ethanol and the ethylcellulose was dissolved in the myvacet solution and applied at a rate of 20-25 g/minute until 2600 g of coating solution had been applied.

The present invention may be incorporated into a pharmaceutical composition and include immediate release, extended release or delayed release compositions. The present invention relates to oral administration of cationic exchange resin drug complex, although other delivery methods are also contemplated, e.g., topical, rectal, injectable, subcutaneous, vaginal or nasal administration. The pharmaceutical compositions of the present invention can take the form of tablets, powders, capsules, gels, hydro-gels, solids, lyophilized suspensions, liquid suspensions or other conventional dosage forms. The present pharmaceutical composition may also be provided in a variety of dosage forms, e.g., solution, suspension, cream, ointment, lotion, capsule, caplet, softgel, gelcap, suppository, enema, elixir, syrup, emulsion, film, granule, gum, insert, jelly, foam, paste, pastille, pellet, spray, troche, lozenge, disk, magma, poultice, or wafer and the like. In addition the resin-drug complex of the present invention is suitable for dosages varying over a wide range, e.g., from about 0.01 to about 2000 mg, depending on the nature of the drug, resin and its intended usage.

In addition the present invention may include other additives conventionally used in pharmaceutical compositions and known to those of skill in the art, e.g., anti-adherents, anti-sticking agents, glidants, flow promoters, lubricants, talc, magnesium stearate, fumed silica), micronized silica, surfactants, waxes, stearic acid, stearic acid salts, stearic acid derivatives, starch, hydrogenated vegetable oils, sodium benzoate, sodium acetate, leucine and magnesium lauryl sulfate.

In accordance with the present invention is a method of reducing the handling of a pharmaceutical composition during preparation by contacting one or more grossly wetted cationic exchange resin particles with an active drug and adding about 0.1% to about 5% by weight of sugar alcohol, based on the combined weight of the sugar alcohol, drug substance and the one or more grossly wetted ionic exchange resin particles. Additionally, the pharmaceutical composition can be coated with a water-permeable diffusion barrier.

Example V

| | |
|---|---|
| Purified Water USP | 45.26 Kg |
| Sorbitol USP | 9.59 Kg |
| Amberlite IRP69 | 16.50 Kg |
| Dextromethorphan HBr USP | 16.50 Kg |

In Example V, the water, sorbitol, drug and resin are slurried together and sufficient time is allowed for the drug to load onto the resin. When the loading operation is completed the slurry is separated (e.g., filtered or centrifuged) into liquid and solid fractions. Because the sugar alcohol is highly water soluble most of the sugar alcohol remains in the aqueous phase leaving with about 4% sorbitol in the solids. The solids are not washed, but are dried to yield material suitable for coating.

Example VI

| | |
|---|---|
| Purified Water USP | 41.15 Kg |
| Sorbitol USP (70%) | 13.70 Kg |
| Amberlite IRP69 | 16.50 Kg |
| Pseudoephedrine HCl | 16.50 Kg |

In Example VI, the Water, sorbitol, drug and resin are slurried together and time allowed for the drug to load onto the resin. When the loading operation is completed the slurry is separated (e.g., filtered or centrifuged) into liquid and solid fractions. Because the sugar alcohol is highly water soluble most of the sugar alcohol remains in the aqueous phase leaving with about 4% sorbitol in the solids. The solids are not washed, but are dried to yield material suitable for coating. Product from examples V and VI were coated in fluidized bed processing unit using ethylcellulose plasticized with dibutyl sebacate from acetone/alcohol solution. It is recognized that the release profile may be modified by varying the coating level.

Release profiles for Examples V and VI are shown:

| | Example V | Example VI |
|---|---|---|
| 30 min | 43% | 50% |
| 60 min | 47 | 55 |
| 180 min | 53 | 63 |
| 360 min | 57 | 68 |

Table I is a Exemplary table of possible pharmaceutical compounds that may be used in conjunction with available resins. The skilled art will recognize that other compounds may be used with the present invention and that compounds may be modified or the particular chemical group modified in a compound to allow the use of that compound with the present invention.

TABLE I

Pharmaceutical compounds and drug resins:

| Pharmaceutical Compounds | Resins |
|---|---|
| Codeine, Dihydrocodeine, Hydromorphone, Morphine, Pentazocine and Propoxyphene Norephedrine and Pseudoephedrine Dextromethorphan, gauifenesin, phenylephrine Aspirin and Tramadol, naprisin Metoclopramide | Amberlite ® IR-20 |
| Atropine, Ipratropium Bromide and Scopolamine Cyclobenzaprine and Papaverine Salbutamol, Terbutaline and Theophylline Amoxycillin, Ampicillin, Azlocillin, Bacampicillin, Cefamandole, Cefonicid, Cefotaxime, Cefotetan, Cefoxitin, Ceftriaxone, Mezlocillin and Piperacillin | Amberlite ® IRC-50 |
| Bupropion, Nomifensine, and Nortriptyline Cromolyn Valproic Acid and Phenytoin Propranolol Tamoxifen Dehydrocholic Acid, Diflunisal, Ethacrynic Acid, | Amberlite ® IRP-58 |
| Fenoprofen, Furosemide, Gemfibrozil, Ibuprofen, Naproxen, Phenytoin, Probenecid, Sulindac, Theophylline, Salicylic Acid, Acetylsalicylic Acid, Acetophenazine, Amitriptyline, Amphetamine, Benztropine, Biperiden, Bromodiphenhydramine, Brompheniramine, Carbinoxamine, Chlorcyclizine, | Amberlite ® IRP-64 |
| Chlorpheniramine, Chlorphenoxamine, Chlorpromazine, Clemastine, Clomiphene, Clonidine, Codeine, Cyclizine, Cyclobenzaprine, Cyproheptadine, Desipramine, Dexbrompheniramine, Dexchlorpheniramine, Dextroamphetamine, Dicyclomine, Diphemanil, Diphenhydramine, Doxepin, Doxylamine, Ergotamine | Amberlite ® IRP-69 |
| Fluphenazine, Haloperidol, Hydrocodone, Hydroxychloroquine, Hydroxyzine, Hyoscyamine, Imipramine, Levopropoxyphene, Maprotiline, Meclizine, Mepenzolate, Meperidine, Mephentermine, Mesoridazine, Methadone, Methdilazine, Methscopolamine, Methysergide, Metoprolol, Nortriptylene, Noscapine, | Amberlite ® XE-69 |
| Nylindrin, Orphenadrine, Papaverine, Pentazocine, Phendimetrazine, Phentermine, Phenylpropanolamine, Pyrilamine, Tripelennamine, Triprolidine, Promazine, Propoxyphene, Propanolol, Pseudoephedrine, Pyrilamine, Quinidine, Scopolamine, Chlorpheniramine, Codeine, | Amberlite ® IR-120 |
| Aminocaproic Acid, Aminosalicylic Acid, Hydromorphone, Isoxsuprine, Levorphanol, Melphalan, Morphine, Nalidixic Acid, Paraaminosalicylic Acid Phenylpropanolamine (PPA), Dextromethorphan, Ephedrin, Pseudoephedrine, Paraamino Salicyclic Acid, Acetyl Salicylic Acid, Phentermine (Phenyl-Tertiary-Butyl-Amine) and Acetaminophen | Dow ® XYS-40013.00 |
| Acetominophen and Phenacetin | Dow ® XYS-40010.00 |

The samples were evaluated under conditions that simulate those encountered in the gastrointestinal tract. The samples were evaluated using USP Dissolution Apparatus 2 and Simulated Gastric Fluid USP. Additional tests are applied as deemed suitable, i.e. USP Apparatus 4 using Simulated Gastric Fluid or selected buffer solutions. The changes in absorption at the selected wavelength as a function of time was recorded as the drug was released from a drug-resin complex sample.

Table II is a comparison of the release curves in simulated gastric conditions for the present invention and resin complexes made by methods used in the art. In Table I the percent release is charted as a function of time for the present invention (A), a sample made using the post treatment protocol under U.S. Pat. No. 4,847,077 (B) and a sample made using no treatment under the protocol of U.S. Pat. No. 4,996,047 (C). The data represented in Table II demonstrates that while high drug loading can be used to prepare coated, slow release drug resin complex, the use of higher levels of treatment under the '077 patent result in a slower, better controlled release profile. It also shows that much lower levels of treating agent as prepared by the present invention result in comparable, lower release rates.

|  | % Released | | |
|---|---|---|---|
| Time (hours) | A | B | C |
| 0.1 | 14.3 | 18.3 | 19.3 |
| 0.5 | 29.3 | 29.1 | 32.5 |
| 1 | 33.9 | 33.1 | 37.5 |
| 2 | 37.9 | 36.9 | 41.6 |
| 3 | 40.3 | 39.1 | 44.1 |
| 4 | 42.1 | 41.0 | 45.6 |
| 5 | 43.6 | 42.3 | 47.2 |
| 6 | 44.8 | 43.7 | 48.8 |
| 7 | 45.9 | 44.3 | 49.7 |
| 8 | 46.9 | 45.3 | 50.4 |
| 9 | 47.8 | 46.2 | 51.1 |
| 10 | 48.6 | 47.1 | 52.1 |

Table III is a comparison of the relative amounts and combinations of drug and resin complexes of the present invention. Table III is only an exemplar table and the skilled artisan will recognize the numerous combinations of drug and resin complexes.

use of other known active compounds with the present invention, e.g., herbicides, fungicides, insecticides, acaricides, nematicides, bird repellants, plant nutrients and agents that improve soil structure.

Examples of the insecticide, acaricide and nematocide that may be used with the present invention include pyrethroid compounds (e.g., permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin, imiprothrin and 1-ethynyl-2-fluoro-2-pentenyl 3-(2,2-dichlorovinyl)-2,2-dimethylcyclopropan-ecarboxylate); organophosphorus compounds (e.g., cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, metoxadiazone and fenothiocarb); neonicotinoids (e.g., nitroiminoimidazolidine derivatives, nitrovinylidenediamine derivatives [e.g. N-[(6-chloro-3-pyridylmethyl)-N-ethyl-N'-methyl-2-nitrovinylenediamine (common name: nitenpyram)], nitroguanidine derivatives, cyanoacetamidine derivatives, N1-[(6-chloro-3-pyridyl)methyl]-N-2-cyano-N-1-methylacetamidine, cyanoiminothiazolidine derivatives, 1-(2-chloro-5-pyridylmethyl)-2-cyanoiminothiazolidine, nitroiminotetrahydro-1,3,5-oxadiazine derivatives, 3-[(2-chloro-5-thiazolyl)methyl]-5-methyl-4-nitroiminotetrahydro-1,3,5-oxadiazine (common name: thiamethoxam), nitroiminohexahydro-1,3,5-triazine derivatives, 3,5-dim-

| mgs Resin | Drug | | | | |
|---|---|---|---|---|---|
| | PropoxyPhene/ Codeine | Aspirin/ Naproxen/ acetaminophen | DextroMethorphan/ Gauifenesin | Carbinoxamine | PseudoePhedrine/ Phenylephrine |
| IRP-69 80-2000 | 50-1000 | 50-1000 | 50-1000 | 50-1000 | 50-1000 |
| IR-20 80-2000 | 50-1000 | 50-1000 | 50-1000 | 50-1000 | 50-1000 |
| IRC-50 80-2000 | 50-1000 | 50-1000 | 50-1000 | 50-1000 | 50-1000 |
| IRP-58 80-2000 | 50-1000 | 50-1000 | 50-1000 | 50-1000 | 50-1000 |
| IRP-64 80-2000 | 50-1000 | 50-1000 | 50-1000 | 50-1000 | 50-1000 |
| IRP-69 80-2000 | 50-1000 | 50-1000 | 50-1000 | 50-1000 | 50-1000 |
| XE-69 80-2000 | 50-1000 | 50-1000 | 50-1000 | 50-1000 | 50-1000 |
| IR-120 80-2000 | 50-1000 | 50-1000 | 50-1000 | 50-1000 | 50-1000 |
| XYS-40013.00 80-2000 | 50-1000 | 50-1000 | 50-1000 | 50-1000 | 50-1000 |
| XYS-40010.00 80-2000 | 50-1000 | 50-1000 | 50-1000 | 50-1000 | 50-1000 |

In addition to pharmaceutical compounds used in conjunction with available resins the inventors have contemplated the ethyl-1-[(2-chloro-5-thiazolyl)methyl]-2-nitroiminohexahydro-1,3,5-triazine; nereistoxin derivatives (e.g., cartap, bensultap and thiocyclam); chlorinated hydrocarbon compounds (e.g., benzoepin, dicofol and tetradifon; formamidine derivatives (e.g., amitraz and chlordimeform); phenylpyrazole derivatives (e.g., ethiprole); benzoylphenylurea compounds (e.g., diflubenzuron, teflubenzuron, chlorfluazuron, flufenoxuron, triflumuron, hexaflumuron, lufenuron and novaluron); triazine derivatives (e.g., cyromazine); thiadiazine derivatives (e.g., buprofezine); juvenoid compounds (e.g., methoprene, hydroprene, fenoxycarb and diofenolan); tebufenozide; methoxyfenozide; halofenozide; chromafenozide; chlorofenapir; phenisobromolate; quinomethionate; propargit; fenbutatin oxide; hexythiazox; etoxazole; clofentezine; fenpyroximate; tebufenpyrad; pyrimidifen; polynactin complex; milbemectin; avermectin; ivermectin and azadirachtin.

Specific examples of a insecticides include: 2,3,5,6-tetrafluorobenzyl-chrysanthemate; 2,3,5,6-tetrafluorobenzyl-2,2-dimethyl-3-(1-propenyl)cyclopropane carboxylate; 4-methyl-2,3,5,6-tetrafluorobenzyl-chrysanthemate; 4-methyl-2,3,5,6-tetrafluorobenzyl-2,2-dimethyl-3-(2,2-dichlorovinyl) cyclopropane carboxylate; 4-methyl-2,3,5,6-tetrafluorobenzyl-2,2-dimethyl-3-(2,2-difluorovinyl) cyclopropane carboxylate; 4-methoxymethyl-2,3,5,6-tetrafluorobenzyl-chrysanthemate; 4-methoxymethyl-2,3,5, 6-tetrafluorobenzyl-2,2-dimethyl-3-(1-propenyl) cyclopropane carboxylate; 2,3,4,5,6-pentafluorobenzyl-2,2-dimethyl-3-(2-chloro-2-trifluoromethylvinyl)cyclopropane carboxylate; and 4-propargyl-2,3,5,6-tetrafluorobenzyl-3-(1-propenyl)-2,2-dimethylcyclopropane carboxylate. Further, as examples of compounds other than those expressed by formula (I), the following chemicals may be given: 4-methoxymethyl-2,3,5,6-tetrafluorobenzyl-2,2,3,3-tetramethylcyclopropane carboxylate; and 4-propargyl-2,3,5,6-tetrafluorobenzyl-2,2,3,3-tetramethylcyclopropane carboxylate.

Suitable herbicides include: anilides (e.g., diflufenican and propanil), arylcarboxylic acids (e.g., dichloropicolinic acid, dicamba and picloram), aryloxyalkanoic acids (e.g., 2,4-D, 2,4-DB, 2,4-DP, fluroxypyr, MCPA, MCPP and triclopyr), aryloxy-phenoxy-alkanoic esters (e.g., diclofop-methyl, fenoxaprop-ethyl, fluazifop-butyl, haloxyfop-methyl and quizalofop-ethyl), azinones (e.g., chloridazon and norflurazon), carbamates (e.g., chlorpropham, desmedipham, phenmedipham and propham), chloroacetanilides (e.g., alachlor, acetochlor, butachlor, metazachlor, metolachlor, pretilachlor and propachlor), dinitroanilines (e.g., oryzalin, pendimethalin and trifluralin), diphenyl ethers (e.g., acifluorfen, bifenox, fluoroglycofen, fomesafen, halosafen, lactofen and oxyfluorfen), ureas (e.g., chlortoluron, diuron, fluometuron, isoproturon, linuron and methabenzthiazuron), hydroxylamines (e.g., alloxydim, clethodim, cycloxydim, sethoxydim and tralkoxydim), imidazolinones (e.g., imazethapyr, imazamethabenz, imazapyr and imazaquin), nitriles (e.g., bromoxynil, dichlobenil and ioxynil), oxyacetamides (e.g., mefenacet), sulphonylureas (e.g., amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl), thiocarbamates (e.g., butylate, cycloate, di-allate, EPTC, esprocarb, molinate, prosulfocarb, thiobencarb and tri-allate), triazines (e.g., atrazine, cyanazine, simazine, simetryne, terbutryne and terbutylazine), triazinones (e.g., hexazinone, metamitron and metribuzin), others (e.g., aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of preparing an ion exchange resin drug complex comprising the steps of:
   contacting one or more ion exchange resin particles with one or more pharmaceutically active drugs,
   adding about 0.01% to about 10% by weight of one or more sugar alcohols to the one or more ion exchange resin particles and one or more pharmaceutically active drugs, wherein the about 0.01% to about 10% by weight of one or more sugar alcohols is based on the combined weight of the one or more sugar alcohols, one or more pharmaceutically active drugs and the one or more ion exchange resin particles, and wherein the one or more sugar alcohols are distributed throughout the ion exchange resin particles, and
   coating the ion exchange resin particles with a water-permeable diffusion barrier and wherein the weight of sugar alcohol in the coated particles is about 0.01% to about 10% of the combined weight of the one or more sugar alcohols, one or more pharmaceutically active drugs and the one or more ion exchange resin particles.

2. The method of claim 1, wherein the one or more sugar alcohols is selected from the group consisting of mannitol, sorbitol, xylitol, maltitol, lactitol, 1,3-dihydroxypropane, inositol glucose, sucrose or combinations and mixtures thereof.

3. The method of claim 1, wherein the ion exchange resin comprises polymers of dipropylene glycol diallyl ether, polyglycol diallyl ether, triethylene glycol divinyl ether, hydroquinone diallyl ether, tetraallyloxyethanoyl, vinyl ether, vinyl acetate, vinyl butylbenzoate, crontonic acid, polyfunctional alcohol, tetraethylene glycol diacrylate, triallylamine, trimethylolpropane diallyl ether, methylenebisacrylamide, divinylbenzene, phthalic, sulphonphthalic acid, ethylene glycol, polymethyl siloxane $\alpha,\gamma$-hydroxypropyl or combinations thereof.

4. The method of claim 1, wherein the active drug is selected from the group consisting of narcotic analgesics, sympathomimetics, antitussives, analgesics antiemetics, anticholinergics, muscle relaxants, bronchodilators, antibiotics, antidepressants, antiasthmatics, antineoplastics, antiepileptics, cardiovascular agents, mixtures and combinations thereof.

5. The method of claim 1, wherein the active drug is selected from the group consisting of codeine, dihydrocodeine, hydromorphone, morphine, pentazocine, propoxyphene, norephedrine, pseudoephedrine, dextromethorphan, aspirin, tramadol, metoclopramide, atropine, ipratropium bromide, scopolamine, cyclobenzaprine, papaverine, salbutamol, terbutaline and theophylline, amoxicillin, ampicillin, azlocillin, bacampicillin, cefamandole, cefonicid, cefotaxime, cefotetan, cefoxitin, ceftriaxone, mezlocillin, piperacillin, bupropion, nomifensine, nortriptyline, cromolyn, tamoxifen, valproic acid and phenvtoin, propranolol mixtures and combinations thereof.

6. The method of claim 1, wherein the one or more sugar alcohols are 0.1% to 5% by weight.

7. The method of claim 1, wherein the one or more sugar alcohols are sorbitol.

8. The method of claim 1, wherein the one or more sugar alcohols is sorbitol which is 0.1% to 5% by weight.

9. The method of claim 1, further comprising filtering the ion exchange resin drug complex.

10. The method of claim 9, wherein the ion exchange resin drug complex is not washed after the filtration.

11. The method of claim 1, wherein the one or more sugar alcohols are added during the contacting of the one or more pharmaceutically active drugs with the one or more ion exchange resin particles.

12. The method of claim 1, wherein the one or more sugar alcohols are added after the contacting of the one or more pharmaceutically active drugs with the one or more ion exchange resin particles.

* * * * *